United States Patent [19]
Elbe et al.

[11] Patent Number: 5,011,850
[45] Date of Patent: Apr. 30, 1991

[54] SUBSTITUTED DIAZOLYLALKYL-CARBINOLS, A PROCESS FOR THEIR PREPARATION AND THEIR USE AS ANTIMYCOTIC AGENTS

[75] Inventors: Hans-Ludwig Elbe; Erik Regel, both of Wuppertal; Karl H. Büchel, Burscheid; Klaus Schaller, Wuppertal; Manfred Plempel, Haan, all of Fed. Rep. of Germany

[73] Assignee: Bayer Aktiengesellschaft, Leverkusen, Fed. Rep. of Germany

[21] Appl. No.: 915,435

[22] Filed: Oct. 6, 1986

Related U.S. Application Data

[63] Continuation of Ser. No. 578,238, Feb. 8, 1984, abandoned.

[30] Foreign Application Priority Data

Mar. 2, 1983 [DE] Fed. Rep. of Germany ....... 3307218

[51] Int. Cl.$^5$ .................... A61K 31/41; C07D 249/08
[52] U.S. Cl. .................... 514/383; 548/266.6
[58] Field of Search ............... 548/262, 266.6; 514/383

[56] References Cited

U.S. PATENT DOCUMENTS

| | | | |
|---|---|---|---|
| 4,404,216 | 9/1983 | Richardson | 548/262 |
| 4,416,682 | 11/1983 | Worthington | 548/262 |
| 4,472,415 | 9/1984 | Worthington et al. | 514/383 |

*Primary Examiner*—Mary C. Lee
*Assistant Examiner*—Patricia L. Morris
*Attorney, Agent, or Firm*—Sprung Horn Kramer & Woods

[57] ABSTRACT

The invention relates to compounds and their derivatives, said compounds being described herein as those of Formula (I). The compounds and compositions containing them are effective antimycotic agents and the invention includes methods for the use of said compounds and compositions.

15 Claims, No Drawings

SUBSTITUTED DIAZOLYLALKYL-CARBINOLS, A PROCESS FOR THEIR PREPARATION AND THEIR USE AS ANTIMYCOTIC AGENTS

This is a continuation, of application Ser. No. 578,238, filed Feb. 8, 1984, now abandoned.

The present invention relates to substituted diazolylalkyl-carbinols, a process for their preparation and their use as antimycotic agents.

It has already been disclosed that certain diazolyl derivatives have antimycotic properties.

New substituted diazolylalkyl-carbinols of the formula

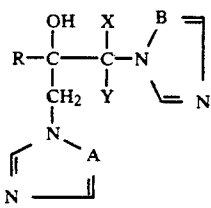  (I)

in which
  A represents a nitrogen atom or the CH group,
  B represents nitrogen atom or the CH group,
  X represents hydrogen or alkyl,
  Y represents alkyl, or alkenyl, alkinyl or optionally substituted benzyl, if X represents hydrogen, and
  R represents optionally substituted phenyl or the grouping

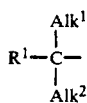

wherein
  Alk$^1$ represents alkyl and
  Alk$^2$ represents alkyl, or
  Alk$^1$ and Alk$^2$ together represent a cycloaliphatic ring, and
  R$^1$ represents alkyl, alkenyl or in each case optionally substituted phenyl, phenylalkyl, phenoxy, phenylthio, phenoxyalkyl, phenylthioalkyl, benzyloxy or benzylthio, and physiologically acceptable acid addition salts thereof, have been found.

The compounds of the formula (I) sometimes have two asymmetric carbon atoms. In this case, they can exist in two geometric isomer forms.

Racemate mixtures can be separated into the pure racemates in a known manner on the basis of the physicochemical differences of the constituents for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

It has furthermore been found that the substituted diazolylalkyl-carbinols of the formula (I) are obtained by a process in which azolyl-oxiranes of the formula

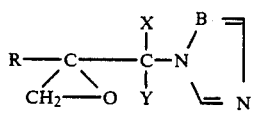  (II)

in which
  B, R, X and Y have the abovementioned meaning, are reacted with azoles of the formula

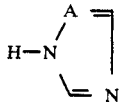  (III)

in which
  A has the abovementioned meaning, in the presence of a diluent and if appropriate in the presence of a base.

If appropriate, an acid can then be added onto the compounds of the formula (I) thus obtained, whereby acid-addition salts are formed The new substituted diazolylalkyl-carbinols of the formula (I) have powerful antimycotic properties.

The new substituted diazolylalkyl carbinols of the formula (I) are also interesting intermediates. Thus, for example, the compounds of the formula (I) can be converted into the corresponding ethers on the hydroxyl group in the customary manner. Acyl or carbamoyl derivatives of the compounds of the general formula (I) can furthermore be obtained by reaction with, for example, acyl halides or carbamoyl chlorides in a manner which is known in principle.

The compounds of the formula (I) in which R$^1$ represents in each case optionally substituted phenylthio, phenylthioalkyl or benzylthio can furthermore be oxidised to the corresponding SO or SO$_2$ derivatives in the customary manner.

Formula (I) provides a general definition of the diazolylalkyl-carbinols according to the invention. Preferably, in this formula,
  A represents a nitrogen atom or the CH group,
  B represents a nitrogen atom or the CH group,
  X represents hydrogen or straight-chain or branched alkyl with 1 to 6 (especially 1 to 3) carbon atoms,
  Y represents straight-chain or branched alkyl with 1 to 6 (especially 1 to 3) carbon atoms; or, if X represents hydrogen, also straight-chain or branched alkenyl or alkinyl with in each case 3 to 6 carbon atoms or benzyl which is optionally mono-, di- or tri-substituted in the phenyl part by identical or different substituents, substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, nitro and cyano; and R represents phenyl which is optionally mono- di- or tri-substituted by identical or different substituents, preferred substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably fluorine and chlorine atoms, nitro, cyano, hydroxyl, hydroxycarbonyl, alkoxycarbonyl with 1 to 4 carbon atoms in the alkyl part, hydroximinoalkyl with 1 to 4 carbon atoms, alkoximinoalkyl with 1 to 4 carbon atoms in each alkyl part and phenyl, phenoxy, benzyl and benzyloxy, each of which is optionally substituted by halogen and/or alkyl with 1 or 2 carbon atoms; or R preferably represents the grouping

wherein

Alk$^1$ represents straight-chain or branched alkyl with 1 to 3 or 4 carbon atoms; and Alk$^2$ represents straight-chain or branched alkyl with 1 or 3 or 4 carbon atoms; or Alk$^1$ and Alk$^2$, together with the carbon atom to which they are bonded, represent a 3-membered to 7-membered cycloaliphatic ring; and R$^1$ represents straight-chain or branched alkyl with 1 to 6 (especially 1 to 3) carbon atoms, alkenyl with 2 to 4 carbon atoms, or phenyl, phenylalkyl with 1 to 4 carbon atoms in the alkyl part, phenoxy, phenylthio, phenoxyalkyl with 1 to 4 carbon atoms in the alkyl part, phenyl- thioalkyl with 1 to 4 carbon atoms in the alkyl part, benzyloxy or benzylthio, each of which is optionally mono-, di- or tri-substituted in the phenyl part by identical or different substituents, preferred possible substituents being the substituents on phenyl already mentioned for R.

Particularly preferred compounds of the formula (I) are those in which

A represents a nitrogen atom or the CH group;

B represents a nitrogen atom or the CH group;

X represents hydrogen or straight-chain or branched alkyl with 1 to 3 or 4 carbon atoms;

Y represents straight-chain or branched alkyl with 1 to 3 or 4 carbon atoms; or, if X represents hydrogen, also allyl, methallyl, propargyl, methylpropargyl or benzyl which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro and cyano;

R represents phenyl which is optionally mono- or di-substituted by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxycarbonyl, hydroximinomethyl, 1-hydroximinoethyl, methoximinomethyl, 1methoximinoethyl and phenyl, phenoxy, benzyl and benzyloxy, each of which is optionally substituted by fluorine, chlorine or methyl; or R represents the grouping

wherein

Alk$^1$ represents methyl or ethyl; and

Alk$^2$ represents methyl or ethyl; and

Alk$^1$ and Alk$^2$, together with the carbon atom to which they are bonded, represent cyclobutyl, cyclopentyl or cyclohexyl; and R$^1$ represents methyl, ethyl, n-propyl, ipropyl, n-butyl, neopentyl, or phenyl, benzyl, phenethyl, phenoxy, phenylthio, phenoxymethyl, phenoxyethyl, phenylthiomethyl, phenylthioethyl, benzyloxy or benzylthio, each of which is optionally mono- or di-substituted in the phenyl part by identical or different substituents, possible substituents being the substituents on phenyl which have already been mentioned for R.

Pharmaceutically acceptable addition salts of acids and those substituted diazolylalkyl-carbinols of the formula (I) in which the substituents A, B, X, Y and R have the meanings which have already been mentioned as preferred for these substituents are also preferred compounds according to the invention.

Preferred acids which can be added on to form pharmaceutically acceptable acid addition salts include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example acetic acid, maleic acid, succinic acid, fumaric acid, tartaric acid, citric acid, salicylic acid, sorbic acid and lactic acid, and sulphonic acids, such as o-toluenesulphonic acid and 1,5-naphthalenedisulphonic acid.

If, for example, 2-(4-chlorophenyl-2-[2-(1,2,4-triazol-1-yl)-2-propyl]-oxirane and 1,2,4-triazol-1-yl)-2-propyl-]oxirane and 1,2,4-triazole are used as starting substances, the course of the process according to the invention can be represented by the following equation:

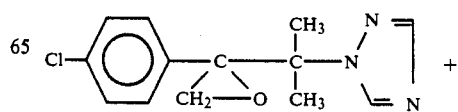

$$H-N\overset{N}{\underset{N}{\underset{\parallel}{\vphantom{|}}}}\Bigg] \longrightarrow Cl-\underset{}{\underset{}{\bigcirc}}-\overset{OH}{\underset{CH_2}{\underset{|}{C}}}-\overset{CH_3}{\underset{CH_3}{\underset{|}{C}}}-N\overset{N}{\underset{N}{\underset{\parallel}{\vphantom{|}}}}\Bigg]$$

$$\underset{N\underset{\parallel}{\underset{N}{\phantom{N}}}}{\underset{|}{N}}$$

Formula (II) provides a general definition of the azolyl-oxiranes to be used as starting substances for carrying out the process according to the invention. In this formula, B, R, X and Y preferably have those meanings which have already been mentioned as preferred for these substituents in connection with the description of the substances of the formula (I) according to the invention.

The azolyl-oxiranes of the formula (II) are not yet known. However, they can be obtained by reacting azolyl-ketones of the formula $$R-CO-\overset{X}{\underset{Y}{\underset{|}{C}}}-N\overset{B}{\underset{N}{\underset{\parallel}{\vphantom{|}}}}\Bigg] \quad (IV)$$

in which

B, R, X and Y have the abovementioned meaning, either (α) with dimethyloxosulphonium methylide of the formula $$\overset{\delta^+}{(CH_3)_2S}\overset{\delta^-}{OCH_2} \quad (V)$$

in a manner which is in itself known, in the presence of a diluent, such as, for example, dimethylsulphoxide, at temperatures between 20° C. and 80° C. (in this context, compare J. Am. Chem. Soc. 87, 1363–1364 (1965)), or (β) with trimethylsulphonium methyl-sulphate of the $$[(CH_3)_3S^+]\,CH_3SO_4^- \quad (VI)$$

in a manner which is in itself known, in the presence of an inert organic Solvent, such as, for example, acetonitrile, and in the presence of a base, such as, for example, sodium methylate, at temperatures between 0° C. and 60° C., preferably at room temperature (compare also Heterocycles 8, (1977)).

If appropriate, the oxiranes of the formula (II) thus obtained can be further reacted directly, without being isolated.

Some of the azolyl-ketones of the formula (IV) are known (compare, for example, British patent. No. 1 464 and DE-OS (German Published Specification) 3,048,266 corresponding to U.S. Ser. No. 328,871 filed Dec. 8, 1981). Azolyl-ketones of the formula $$R-CO-\overset{X^1}{\underset{Y^1}{\underset{|}{C}}}-N\overset{B}{\underset{N}{\underset{\parallel}{\vphantom{|}}}}\Bigg] \quad (Iva)$$

in which $X^1$ represents straight-chain or branched alkyl with 1 to 3 or 4 carbon atoms, $Y^1$ represents straight-chain or branched alkyl with 1 to 3 or 4 carbon atoms and B and R have the meaning given above, are not yet known.

The azolyl-ketones of the formula (Iva) are obtained by reacting halogenoketones of the formula $$R-CO-\overset{X^1}{\underset{Y^1}{\underset{|}{C}}}-Hal \quad (VII)$$

in which

R, $X^1$ and $Y^1$ have the meaning given above and

Hal represents halogen, in particular chlorine or bromine, with azoles of the formula $$H-N\overset{B}{\underset{N}{\underset{\parallel}{\vphantom{|}}}}\Bigg] \quad (VIII)$$

in which

B has the meaning given above, in the presence of a diluent and in the presence of an acid-binding agent.

Possible diluents for the process for the preparation of the azolyl-ketones of the formula (Iva) are inert organic Solvents. These include, preferably, ketones, such as acetone and methyl ethyl ketone; nitriles, such as acetonitrile and propionitrile; alcohols, such as ethanol or isopropanol; ethers, such as tetrahydrofuran or dioxane; aromatic hydrocarbons, such as toluene, benzene or chlorobenzene; formamides, such as dimethylformamide, and halogenated hydrocarbons, such as methylene chloride.

The process for the preparation of the azolylketones of the formula (Iva) is carried out in the presence of an acid-binding agent. All the inorganic and organic acid-binding agents which are generally employed can be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine and N,N-dimethylbenzylamine, and furthermore pyridine and diazabicyclooctane. An appropriate excess of azole is preferably used.

The reaction temperatures can be varied within a substantial range in the process for the preparation of the azolyl-ketones of the formula (Iva). In general, the reaction is carried out between about 20° and 150° C., preferably at 40° to 100° C.

In carrying out the process for the preparation of the azolyl-ketones of the formula (Iva), 1 to 4 moles of azole and 1 to 4 moles of acid-binding agent are preferably employed per mole of halogenoketone of the formula (VIII). The azolyl-ketones of the formula (IVa) are isolated in the customary manner.

The halogenoketones of the formula (VII) are known in some cases (compare Synth. Commun. 12 (1982), pages 261–266), or they can be obtained in a generally known manner, for example by reacting the corresponding ketones of the formula

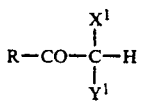  (IX)

in which
R, $X^1$ and $Y^1$ have the meaning given above, with chlorine or bromine in the presence of an inert organic solvent, such as, for example, chlorinated hydrocarbons, at room temperature; or with customary chlorinating agents, such as, for example, sulphuryl chloride, at temperatures between 20° and 60° C.

The new azolyl-ketones of the formula (IVa) not only are interesting intermediates, but also themselves display good antimycotic properties. When applied in certain amounts, azolyl-ketones of the formula (IVa) can also be used as plant protection agents.

Possible diluents for the process according to the invention are organic solvents which are inert under the reaction conditions. These include, preferably, alcohols, such as, for example, ethanol, methoxyethanol, isopropanol or propanol; ketones, such as, for example, acetone, methyl ethyl ketone or 2-butanone; nitriles, such as, for example, acetonitrile; esters, such as, for example $C_1$–$C_6$-alkyl esters of $C_1$–$C_6$-alkanoic acid esters, for example, ethyl acetate; ethers, such as for example, dioxane; nitriles, such as, for example, acetonitrile; esters, such as, for example, ethyl acetate, ethers, such as for example, dioxane; aromatic hydrocarbons, such as, for example, benzene and toluene; and amides, such as, for example, dimethylformamide.

Possible bases for the reaction according to the invention are all the inorganic and organic bases which can usually be employed. These include, preferably, alkali metal carbonates, such as, for example, sodium and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the process according to the inventing. In general, the reaction is carried out at temperatures between 0° and 200° C., preferably between 60° and 150° C.

In carrying out the process according to the invention, 1 to 2 moles of azole of the formula (III) and, if appropriate, 1 to 2 moles of base are preferably employed per mole of oxirane of the formula (II); the end products are isolated in the generally customary manner.

The compounds of the formula (I) according to the invention can also be obtained by a process in which diazolyl-ketones of the formula

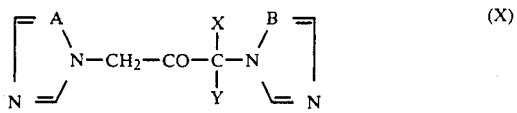  (X)

in which
A, B, X and Y have the abovementioned meaning, are reacted with a Grignard reagent of the formula

  (XI)

in which
R has the abovementioned meaning and
Hal' represents halogen, under the conditions of a Grignard reaction in the customary manner; or in which dihalogenoalkanols of the formula

  (XII)

in which
R, Hal, X and Y have the abovementioned meaning, are reacted with azoles of the formula (III) in the customary manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an organic solvent.

The compounds of the formula (I) which can be used according to the invention and their acid addition salts display antimicrobial actions, in particular powerful antimycotic actions. They possess a very broad antimycotic action spectrum, especially against dermatophytes and blastomyces as well as biphase fungi, for example against varieties of Candida, such as Candida albicans, varieties of Epidermophyton, such as Epidermophyton floccosum, varieties of Aspergillus, such as Aspergillus niger and Aspergillus fumigatus, varieties of Trichophyton, such as Trichophyton mentagrophytes, varieties of Microsporon, such as Microsporon felineum and varieties of Torulopsis, such as Torulopsis glabrata. The listing of these micro-organisms in no way implies a limitation of the germs which can be combated but is only of illustrative character.

Examples which may be mentioned of fields of indication in medicine are: dermatomycoses and systemic mycoses caused by Trichophyton mentagrophytes and other varieties of Trichophyton, varieties of Microsporon, Epidermophyton floccosum, blastomyces and biphase fungi as well as moulds.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third of a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, or example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in medicine, for the treatment of the abovementioned diseases.

The active compounds or the pharmaceutical formulations can be administered locally, orally, parenterally, intraperitoneally and/or rectally, preferably parenterally, and in particular intravenously.

In general, it has proved advantageous both in the active compound or compounds according to the invention in total amounts of about 10 to about 300, preferably 50 to 200, mg/kg of body weight every 24 hours, optionally in the form of several individual administrations, in order to achieve the desired results.

However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

PREPARATION EXAMPLES
EXAMPLE 1

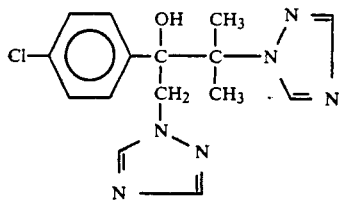

3.6 g (0.052 mole) of 1,2,4-triazole are added to a solution of 0.11 g (0.047 mole) of sodium in 30 ml of n-propanol at room temperature, while stirring. The mixture is heated to the reflux temperature and a solution of 2-(4-chlorophenyl)-2-[2-(1,2,4-triazol-1-yl)prop-2-yl]-oxirane in 20 ml of n-propanol is added. The reaction mixture is heated under reflux for 15 hours and then cooled and poured onto water. The mixture is extracted with methylene chloride and the organic phase is dried over sodium sulphate and concentrated. The residue is purified by column chromatography (silica gel; chloroform:methanol=9:1). 3.7 g (24.2% of theory) of 2-(4-chlorophenyl)-1,3-di-(1,2,4-triazol-1-yl)-3-methyl-2-butanol of melting point 114° C. are obtained.

Preparation of the starting substance

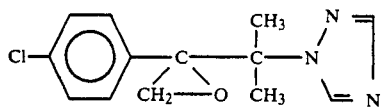

9.6 g (0.044 mole) of trimethylsulphonium iodide are dissolved in 9.6 g (0.118 mole) of dimethyl sulphate under a nitrogen atmosphere. 5.2 g (0.044 mole) of potassium tert.-butylate are added at room temperature and the mixture is subsequently stirred at room temperature for 6 hours. A solution of 9.9 g (0.0397 mole) of 4-chlorophenyl 2-(1,2,4-triazol-1-yl)-prop-2-yl ketone in 16 ml of tetrahydrofuran is then added dropwise at room temperature. The reaction mixture is subsequently led at room temperature for 15 hours and under reflux for 4 hours, cooled and filtered. The filtrate is concentrated in vacuo, the residue is discharged onto water and the mixture is extracted with methylene chloride. The organic phase is dried over sodium sulphate and concentrated in vacuo. 10.4 g (100% of theory) of 2-(4-chlorophenyl-2-[2-(1,2,4-triazol-1-yl)-prop-2-yl]-oxirane of refractive indes $n_D^{20}$ 1.5388 are obtained.

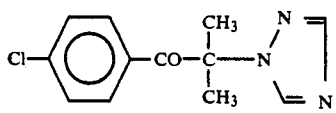
(Iva-1)

80 g (0.31 mole) of 2-bromo-prop-2-yl 4-chlorophenyl ketone, 26.9 g (0.39 mole) of 1,2,4-triazole and 53.8 g (0.39 mole) of potassium carbonate are heated under reflux in 350 ml of acetone for 6 hours. The mixture is allowed to cool and is filtered and the filtrate is concentrated in vacuo. The residue is taken up in methylene chloride and the mixture is washed with water, dried over sodium sulphate and concentrated in vacuo. The residue is recrystallised from diisopropyl ether. 19.9 g (25.7% of theory) of 4-chlorophenyl 2-(1,2,4-triazol-1-yl)-prop-2-yl ketone of melting point 111° C. are obtained.

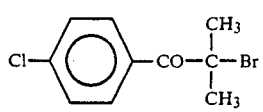

65.5 g (0.36 mole) of 4-chlorophenyl isopropyl ketone are dissolved in 200 ml of chloroform, and 1 ml of hydrogen bromide/glacial acetic acid is added. 57.5 g (0.36 mole) of bromine are then slowly added dropwise at 30° C. and the mixture is subsequently stirred at room temperature for 30 minutes. The mixture is concentrated in vacuo to give 86.6 g (92% of theory) of crude 2-bromo-prop-2-yl 4-chlorophenyl ketone as an oil, which is further reacted directly.

EXAMPLE 2

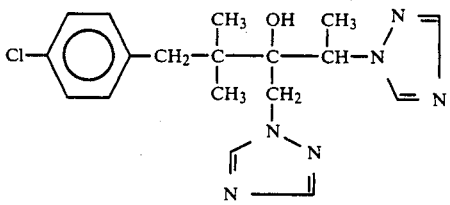

3.6 g (0.052 mole) of 1,2,4-triazole are added to a solution of 0.1 g (0.043 mole) of sodium in 30 ml of n-propanol at room temperature, while stirring. A solution of 13.2 g (0.043 mole) of 2-(4-chlorophenyl-tert.-butyl)-2-[1-(1,2,4-triazol-1-yl)-ethyl]-oxirane in 20 ml of n-propanol is then added. The reaction mixture is heated under reflux for 20 hours and then cooled and poured onto 300 ml of water. The mixture is extracted with methylene chloride and the methylene chloride phase is washed with water, dried over sodium Sulphate and concentrated in vacuo. The residue is purified by column chromatography (silica gel; ethyl acetate:ether=3:1). 4 g (24.8% of theory) of 1-(4-chlorophenyl)-2,2-dimethyl-3-(1,2,4-triazol-1-yl)-methyl)-4-(1,2,4-triazol-1-yl)-3-pentanol of melting point 59° C. are obtained.

Preparation of the starting substance

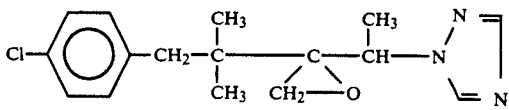

A solution of 9.8 g (0.77 mole) of dimethyl sulphate and 5.3 g (0.085 mole) of dimethyl sulphide in 50 ml of acetonitrile is stirred at room temperature for 5 days. A solution of 13 g (0.044 mole) of 4-chlorophenyl-tert.butyl 1-(1,2,4-triazol-1-yl)-ethyl ketone in 20 ml of acetonitrile is then added dropwise at room temperature. At the same temperature, 4.8 g (0.088 mole) of sodium methylate are introduced and the mixture is subsequently stirred for 20 hours and then concentrated in vacuo. The residue is stirred overnight with a mixture of 35 ml of ethyl acetate and 25 ml of water. The organic phase is separated off, dried over sodium sulphate and concentrated in vacuo. 13.2 g (98.2% of theory) of 2-(4-chlorophenyl-tert.-butyl)-2-[1-(1,2,4-triazol-1-yl)-ethyl]oxirane of refractive index $n_D^{20}$ 1.5431 are obtained.

The following compounds of the general formula

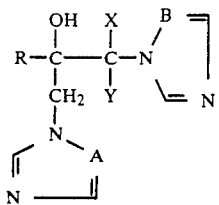

are obtained in a corresponding manner:

| Example No. | R | X | Y | A | B | Melting point (°C.) or $n_D^{20}$ |
|---|---|---|---|---|---|---|
| 3 | F—⌬— | CH₃ | CH₃ | N | N | 56 |
| 4 | ⌬— | CH₃ | CH₃ | N | N | 156 |
| 5 | Cl—⌬—O—⌬— | CH₃ | CH₃ | N | N | 202 |
| 6 | Cl—⌬—⌬— | CH₃ | CH₃ | N | N | 185–90 |
| 7 | F—⌬— | CH₃ | CH₃ | CH | N | 196 |
| 8 | Cl—⌬—O—⌬— | CH₃ | CH₃ | CH | N | 90–100 |
| 9 | Cl—⌬—⌬— | CH₃ | CH₃ | CH | N | 100–10 |
| 10 | ⌬—⌬— | H | CH₃ | N | N | vitreous |
| 11 | Cl—⌬(Cl)— | H | CH₃ | N | N | 143–145 |
| 12 | (CH₃)₃C— | H | CH₃ | N | N | 110 |
| 13 | F—⌬— | H | CH₃ | N | N | 96–99 |

-continued

| Example No. | R | X | Y | A | B | Melting point (°C.) or $n_D^{20}$ |
|---|---|---|---|---|---|---|
| 14 | 4-Cl-C6H4-C(cyclobutyl)- | H | CH3 | N | N | 47 |
| 15 | 4-F-C6H4-CH2-C(CH3)2- | H | CH3 | N | N | 36 |
| 16 | 4-Cl-C6H4-C(CH3)2- | H | CH3 | N | N | 52 (Form A) |
| 17 | 4-Cl-C6H4-C(CH3)2- | H | CH3 | N | N | 60 (Form B) |
| 18 | 2,4-Cl2-C6H3- | H | -CH2-C6H4-Cl (4-) | N | N | 126 |
| 19 | " | H | -CH2-CH=CH2 | N | N | 144 |
| 20 | " | H | -C4H9-n | N | N | 154 |
| 21 | " | H | -C2H5 | N | N | 110 |
| 22 | " | CH3 | CH3 | N | N | 90 |
| 23 | 3,4-Cl2-C6H3- | CH3 | CH3 | N | N | 78 |
| 24 | 2,3-Cl2-C6H3- | CH3 | CH3 | N | N | 138 |
| 25 | 3-Cl-4-F-C6H3-CH2-C(CH3)2- | H | CH3 | N | N | 64–67 |

The following intermediates of the general formula

(IVa)

are obtained according to Example 1 and according to the process conditions described.

| Example No. | R | $X^1$ | $Y^1$ | B | Melting (°C.) point (°C.) or $n_D^{20}$ |
|---|---|---|---|---|---|
| (IVa-2) | 4-F-C6H4- | CH3 | CH3 | N | 104 |
| (IVa-3) | 4-Cl-C6H4-C6H4- | CH3 | CH3 | N | 145–50 |
| (IVa-4) | 4-Cl-C6H4-O-C6H4- | CH3 | CH3 | N | 112 |
| (IVa-5) | C6H5-C6H4- | CH3 | CH3 | N | 140–45 |
| (IVa-6) | C6H5- | CH3 | CH3 | N | 132 |
| (IVa-7) | 4-F-C6H4- | CH3 | CH3 | CH | 1.5273 |
| (IVa-8) | 4-Cl-C6H4-O-C6H4- | CH3 | CH3 | CH | 1.5751 |
| (IVa-9) | 4-Cl-C6H4-C6H4- | CH3 | CH3 | CH | 140 |
| (IVa-10) | 4-Cl-C6H4- | CH3 | CH3 | CH | 1.5505 |
| (IVa-11) | C6H5- | CH3 | CH3 | CH | 1.5445 |
| (IVa-12) | 3,4-Cl2-C6H3- | CH3 | CH3 | N | |
| (IVa-13) | 3,4-Cl2-C6H3- | CH3 | CH3 | CH | |

-continued

| Example No. | R | $X^1$ | $Y^1$ | B | Melting (°C.) point (°C.) or $n_D^{20}$ |
|---|---|---|---|---|---|
| (IVa-14) | 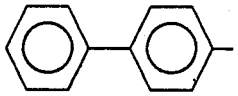 | CH$_3$ | CH$_3$ | CH | |
| (IVa-15) | 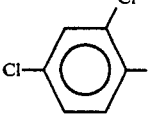 | CH$_3$ | CH$_3$ | N | viscous oil |
| (IVa-16) | 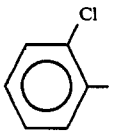 | CH$_3$ | CH$_3$ | N | viscous oil |

EXAMPLE A

Antimycotic in vitro activity

Description of the experiment

The in vitro tests were carried out in a series dilution test with germ inocula of on average $5 \times 10^4$ germs/ml of substrate. The nutrient medium used was
(a) for dermatophytes and moulds: Sabourand's milieu d'épreuve, and
(b) for yeasts: meat extract/glucose broth.

The incubation temperature was 20° C. and the duration of incubation was 24 to 96 hours in the case of yeasts and 96 hours in the case of dermatophytes and moulds.

In this test, the compounds of preparation examples 3, 5, 6, 8, 9 and 10, in particular, show a good antimycotic action spectrum.

TABLE A

Antimycotic in vitro activity
MIC values in γ/ml of nutrient medium for

| Active compound | Tricho-phyton mentagr. | Candida albicans | Torulop-sis glabrata | Aspergillus fumigatus |
|---|---|---|---|---|
| Compounds according to preparation example | | | | |
| 3 | 16 | 16 | 64 | >64 |
| 5 | ≦1 | 2 | 32 | >64 |
| 6 | ≦1 | 64 | — | 16 |
| 8 | 8 | 4 | 32 | 64 |
| 9 | 4 | 8 | 8 | 32 |
| 10 | 2 | 2 | 64 | 64 |

EXAMPLE B

Antimycotic in vivo activity (oral) in candidosis of mice

Description of the experiment:

Mice of the SPF-CF$_1$ type were infested intravenously with $1-2 \times 10^6$ logarthmically growing Candida cells, which were suspended in physiological saline solution. The animals were treated with, in each case, 10–50 mg/kg of body weight of the products one hour before and seven hours after the infection.

Result:

Untreated animals died 3 to 6 days after infection. The survival rate on the 6th day after infection was about 5% in the case of untreated control animals.

In this test, for example, the compounds of preparation examples 1, 3, 4 and 5 showed a good antimycotic action.

| Explanation of symbols | | |
|---|---|---|
| + + + + + = very good action | = | 90% survivors on the 6th day after infection |
| + + + + = good action | = | 80% survivors on the 6th day after infection |
| + + + = action | = | 60% survivors on the 6th day after infection |
| + + = weak action | = | 40% survivors on the 6th day after infection |
| + = trace of action | = | |
| n.a. = no action | | |

TABLE B

Antimycotic in vivo activity (oral) in candidosis of mice
Compounds according to preparation example

| 1 | + + + + + |
| 3 | + + + + + |
| 4 | + + + + + |
| 5 | + + + + |

Example/formulations

| 1. Solution | |
|---|---|
| Active compound according to formula (I): | 10 g |
| Alcohol, pure (96% strength): | 300 g |
| Isopropyl myristate: | 526 g |
| | 836 g |
| 2. Cream | |
| Active compound according to formula (I): | 10 g |
| Arlacel 60: (Sorbitan monostearate) | 20 g |
| Tween 60: (polyoxyethylene(20)-sorbitan monostearate) | 15 g |
| Spermaceti, artificial: (mixture of esters of saturated C$_{14}$-C$_{18}$-fatty acids and C$_{14}$-C18-fatty alcohols) | 30 g |
| Lanette 0: (mixture of cetyl alcohol and stearyl alcohol) | 100 g |
| Entanol G: (2-octyl-dodecanol) | 135 g |
| Benzyl alcohol: | 10 g |

| Water, demineralised: | 680 g |
|---|---|
| | 1,000 g |

We claim:
1. A substituted diazolylalkyl-carbinol of the formula

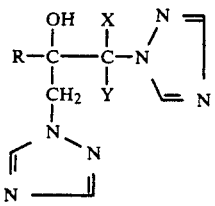

in which
X represents hydrogen or methyl,
Y represents straight-chain or branched alkyl with 1 to 4 carbon atoms, and
R represents phenyl or phenyl which is mono- or di-substituted by identical or different substituents selected from fluorine, chlorine, methyl, trifluoromethoxy, phenyl, chlorophenyl and chlorophenoxy, or
R represents the grouping

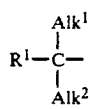

wherein
$Alk^1$ is methyl, and
$Alk^2$ is methyl, or
$Alk^1$ and $Alk^2$, together with the carbon atom to which they are bonded, represent cyclobutyl,
$R^1$ represents methyl, chlorophenyl or benzyl which is mono-or di-substituted in the phenyl part by identical or different substituents selected from fluorine and chlorine.

2. A compound of claim 1 which is 2-(4-chlorophenyl)-1,3-di-(1,2,4-triazol-1-yl)-3-methyl-2-butanol or a pharmaceutically acceptable acid addition salt thereof.

3. A compound of claim 1 which is 2-(4-fluorophenyl)-1,3-di-(2,3,4-triazol-1-yl)-3-methyl-2-butanol or a pharmaceutically acceptable acid addition salt thereof.

4. A compound of claim 1 which is a 2-phenyl-1,3-di(1,2,4-triazol-1-yl)-3-methyl-2-butanol or a pharmaceutically acceptable acid addition salt thereof.

5. A compound of claim 1 which is 2-(4-chlorophenoxyphenyl)-1,3,-di-(1,2,4-triazol-1-yl)-3-methyl-2-butanol.

6. A compound of the formula

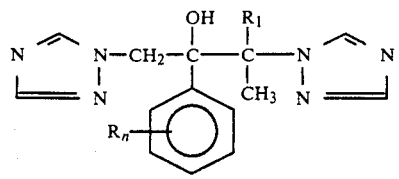

wherein
R is a halogen and n=1 or 2;
$R_1$ is hydrogen or $CH_3$, and physiologically acceptable salt thereof.

7. A pharmaceutical composition containing as an active ingredient, an antimycotically effective amount of a compound according to claim 1 in admixture with an inert carrier.

8. A pharmaceutical composition containing as an active ingredient an antimycotically effective amount of a compound according to claim 1 in the form of a sterile or physiologically isotonic aqueous solution.

9. A composition according to claim 8 containing from 0.5 to 90% by weight of the said active ingredient.

10. A medicament in dosage unit form comprising an antimycotically effective amount of a compound according to claim 1 and an inert pharmaceutical carrier.

11. A medicament of claim 10 in the form of tablets, pills, dragee, capsules, ampules or suppositories.

12. A method of treating of mycoses in warm-blooded animals which comprises administering to the animals an antimycotically effective amount of a compound according to claim 1, either alone or in admixture with an inert carrier or in the form of a medicament.

13. A method according to claim 12 in which the active compound is administered in an amount of about 10 to about 300 mg/kg body weight per day.

14. A method according to claim 13 in which the active compound is administered orally, topically, or parenterally.

15. A method of treating mycosis in an animal host which comprises administering to said host an antimycotically effective amount of a compound of the formula

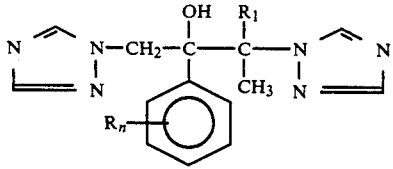

wherein
R is a halogen,
n=1 or 2,
$R_1$ is hydrogen or $CH_e$
and pharmaceutical acceptable salts thereof.

* * * * *

UNITED STATES PATENT AND TRADEMARK OFFICE
CERTIFICATE OF CORRECTION

PATENT NO. : 5,011,850

DATED : April 30, 1991

INVENTOR(S) : Elbe et al.

It is certified that error appears in the above-identified patent and that said Letters Patent is hereby corrected as shown below:

Col. 21, claim 3 line 2   Delete " (2,3, " and substitute -- (1,2, --

Col. 22, line 57   Delete " $CH_e$ " and substitute -- $CH_3$ --

Signed and Sealed this

Fourth Day of May, 1993

Attest:

MICHAEL K. KIRK

*Attesting Officer*   *Acting Commissioner of Patents and Trademarks*